United States Patent [19]

Forster et al.

[11] 4,029,748

[45] June 14, 1977

[54] IRIDIUM CARBONYL COMPLEXES

[75] Inventors: Denis Forster, University City; Arnold Hershman, Creve Couer; Donald E. Morris, Kirkwood, all of Mo.

[73] Assignee: Monsanto Company, St. Louis, Mo.

[22] Filed: July 29, 1974

[21] Appl. No.: 492,958

[52] U.S. Cl. .................................. 423/418; 423/417
[51] Int. Cl.$^2$ .......................................... C01G 1/04
[58] Field of Search ....................... 423/416, 417, 418

[56] References Cited

UNITED STATES PATENTS 3,816,337  6/1974  Usami et al. ...................... 423/418
3,855,396  12/1974 Kniese et al. ...................... 423/418

OTHER PUBLICATIONS

L. Malatesta et al., *J. Chemical Society*, 961–965, (1964).
D. Forster, *Inorganic Chemistry*, 11, 473–475, (1972).

Primary Examiner—Earl C. Thomas
Assistant Examiner—Wayne A. Langel
Attorney, Agent, or Firm—Joseph D. Kennedy; John D. Upham

[57] ABSTRACT

The complexes $[Ir(CO)_3I]$, $[HIr(CO)_3I_2]$, $[HIr(CO)_2I_2(H_2O)]$, $[RIr(CO)_2I_2]$, $[(RCO)Ir(CO)_2I_2]$ where R is an alkyl radical, are described. Processes for preparing the aforesaid complexes are described and in addition a new process for preparation of $[Ir(CO)_3I_3]$ is described.

3 Claims, No Drawings

IRIDIUM CARBONYL COMPLEXES

The present invention relates to novel iridium complexes and to processes for preparing said complexes.

Metal carbonyl halides and their derivatives have been used extensively as carbonylation catalysts. It is an object of the present invention to provide novel iridium carbonyl iodides and derivatives thereof which are particularly active and stable carbonylation catalysts.

Another object of this invention is to provide processes for the preparation of said novel complexes. Examples of such complexes are the compounds of the formulae: $[Ir(Co)_3I]$, $[HIrI_2(Co)_3]$, $[HIrI_2(Co)_2]$, $[RIrI_2(Co)_2]$ $[HIrI_2(Co)_2(H_2O)]$ and $[RCO)IrI_2(CO)_2]$ where R = alkyl preferably having 1 to 20 carbon atoms.

The starting materials from which the above compounds are prepared are complexes of the type [iridium(diene)I] and [iridium (diene)I$_3$]. The complex [iridium(cyclooctadiene)I] is especially useful for the preparation of several of the novel compositions of matter described herein. [Iridium(cyclooctadiene)I] can be prepared by the technique described for the analogous chloro-complex by Winkhaus and Singer Chemische (Berichte, 99, 3610 (1966). [Iridium(cyclooctadiene)I$_3$] is then prepared by addition of iodine to a solution of [iridium(cyclooctadiene)I] in methylene chloride.

The process for preparing the new compositions are summarized in the accompanying Flowsheet. The reactions are most conveniently performed in inert solvents such as hydrocarbons e.g. hexane, benzene, and toluene; halohydrocarbons e.g. methylene chloride, chloroform and chlorobenzene and carboxylic acids such as acetic, propionic, butyric, hexanoic, nonanoic and decanoic acids. The resulting solutions can then be directly used in catalytic processes utilizing soluble catalysts such as hydrocarboxylation reactions. When the catalyst are used for hydrocarboxylation, the preferred solvents for preparing the complexes are carboxylic acids.

As can be observed in the Flowsheet, below, the compound $[Ir(CO)_3I_3]$ is a key intermediate in the preparation of several of the new compositions described herein. The compound $[Ir(CO)_3I_3]$ has been previously described (L. Malatesta, L. Naldini and F. Cariati, *J. Chemical Society*, 961 (1964)) but the preparation which was used involved a reaction conducted at a carbon monoxide pressure of 200 kg/cm$^2$ at elevated temperatures. There is described herein a new process for preparation of this compound which requires much milder conditions of pressure and temperature.

Other diolefins may also be used in the preparation of the iridium carbonyl complexes of the present invention as exemplified below:
Cycloocta-1-5-diene
Norbornadiene
Cycloocta tetraene
1,5-hexadiene
Cyclohexa-1,3-diene 2,5-dimethylhexa-1,5-diene

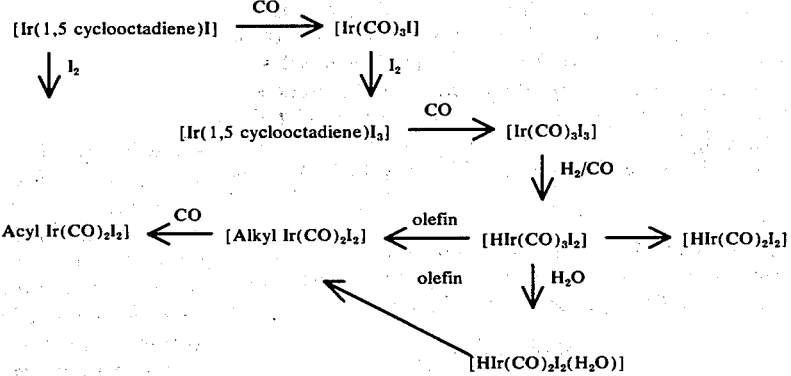

Flow Sheet

The new compositions all contain carbonyl groups bound to the metal atom, and are most conveniently characterized by examination of the infrared spectrum of the solutions which show very strong C ≡ O stretching frequencies.

The invention will be further illustrated by reference to the following examples, which are however not limitative of the scope of the invention.

EXAMPLE 1

Preparation of [Ir(cyclooctadiene)I]

A mixture of 2.6g of IrI$_3$.3H$_2$O, water (24 ml), ethanol (48 ml) and 1,5 cyclooctadiene (4.0 ml) is refluxed for 16 hours under nitrogen at atmospheric pressure at about 80° C. The resulting solution is cooled to 0° C and the brown precipitate which forms is filtered off, washed with methanol, and dried in vacuo. Elemental analysis shows the compound to be iridium (cyclooctadiene) iodide.

EXAMPLE 2

Preparation of [Ir(cyclooctadiene)I$_3$],

A solution of iodine (1.4g) in methylene chloride (30 ml) is added to a stirred mixture of 0.9g of [Ir(cyclooctadiene)I], methylene chloride (10 ml), and cyclooctadiene (1 ml). The mixture is stirred for 20 min. and the resulting black powder is filtered off, washed with ethanol and air-dried.

EXAMPLE 3

Preparation of $[Ir(CO)_3I]$

[Ir(cyclooctadiene)I] in the amount of 0.1g and nonanoic acid (5 ml) are charged to a glass vessel capable of withstanding moderate pressures. The vessel is charged to 4 atomspheres pressure of carbon monoxide and the mixture stirred for 10 minutes at about 40° C. After this time the pressure is released and the brown solution examined on an infrared spectrometer. The new species exhibits C ≡ O stretching bands at 2076 cm$^{-1}$ and 2042 cm$^-$. The new species upon treatment with Bu$_4$N$^+$I$^-$ evolves 1 mole of carbon monoxide per mole of iridium and gives the previously characterized compound [Bu$_4$N] [Ir(CO)$_2$I$_2$], hence proving the presence of three carbonyl groups in the new species.

EXAMPLE 4

Preparation of [Ir(CO)$_3$I$_3$]

Method A

A starting proportion of 0.1g of Ir(cyclooctadiene)I$_3$ and methylene chloride (5 ml) are charged to a small glass vessel capable of withstanding moderate pressures, and heated at 100° C under 3 atmospheres of carbon monoxide pressure for 10 minutes. The vessel is then cooled and depressurized and the resulting orange solution examined on an infrared spctrometer. The solution displays C ≡ O stretching bands at 2186 (weak), 2170 (very weak) and 2132 (very strong).

Method B

A solution of [Ir(CO)$_3$I] prepared as described in Example 3 is treated with a slight excess of iodine, whereupon [Ir(CO)$_3$I$_3$] forms immediately.

EXAMPLE 5

Preparation of [HIr(CO)$_3$I$_2$]

A solution of [Ir(CO)$_3$I$_3$] prepared as described in Example 4 is reacted with a gaseous mixture of carbon monoxide and hydrogen (1:1) under a pressure of 6.3 kg/cm$^2$ at 100° C (in other experiments the Co:H$_2$ molar ratio can be varied from 100:1 to 1:100 ). After 15 minutes the mixture is cooled and the pressure released. The resulting pale-yellow solution of [HIr(CO)$_3$I$_2$] displays C ≡ O stretching bands in its infrared spectrum at 2184 cm$^{-1}$ (weak) and 2123 cm$^{-1}$ (very strong). Treatment of the solution with a molar equivalent of Bu$_4$N$^+$I$^-$ results in evolution of one mole of carbon monoxide per mole of iridium and formation of the [HIr(CO)$_2$I$_3$]$^-$ which has been characterized previously D. Forster, *Inorganic Chemistry* 11, 473 (1972)), confirming the formulation of the new compound.

EXAMPLE 6

Preparation of [HIr(CO)$_2$I$_2$]

A solution of [HIr(CO)$_3$I$_2$] is prepared as described in Example 5 and then nitrogen is flushed through the solution for about 30 minutes at room temperature. An orange compound forms with an infrared spectrum display C ≡ O stretching bands at 2120 cm$^{-1}$ (strong) and 2080 cm$^{116\ 1}$ (strong) with a weak Ir-H stretching band at 2180 cm$^{-1}$. Treatment of solutions containing this new compound with Bu$_4$N$^+$I$^-$ results in formation of the [HIr(CO)$_3$I$_3$]$^-$ ion without evolution of any carbon monoxide and hence the new compound is formulated as [HIr(CO)$_2$I$_2$].

EXAMPLE 7

Preparation of [HIr(CO)$_2$I$_2$(H$_2$O)]

A solution of [HIr(CO)$_3$I$_2$] is prepared in nonanoic acid as described in Example 5 and then water is added to the solution (H$_2$0:Ir ration about 1 although in other experiments this ration varies from 1:1 to 5:1 moles of water per mole of iridium compound). The solution immediately turns an intense blood-red color and this new species exhibits an infrared spectrum with CO stretching frequencies at 2155 cm$^{-1}$ (weak) and 2098 (very strong). This new species reacts with Bu$_4$N$^+$I$^-$B and also gives the [HIr(CO)$_2$I$_3$]$^-$ ion and hence the new species is [HIr(CO)$_2$I$_2$(H$_2$O)].

EXAMPLE 8

Preparation of (RIr(CO)$_2$I$_2$] (where R = alkyl)

Method A

A solution of [HIr(CO)$_3$I$_2$] is prepared as described in Example 5 and then treated with excess of an olefin of formula

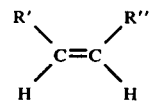

where R' and R'' = H or an alkyl group of 1 to 20 carbon atoms, specifically with R' and R'' being hexyl and in another experiment R' and R'' being dodecyl. A new compound is formed, within 1 minute with α-olefins and over a period of hours with internal olefins, which has an infrared spectrum with strong Co stretching frequencies at 2116 cm$^{-1}$ and 2069 cm$^{-1}$. This new compound upon treatment with Bu$_4$N$^+$I$^-$ gives the previously characterized [RIr(CO)$_2$I$_3$]$^-$ ion and hence the new species is [RIr(CO)$_2$I$_2$].

Method B

A solution of [HIr(CO)$_2$I$_2$(H$_2$O)] prepared by the method outlined in Example 7 when treated with an olefin also gives rise to [RIr(CO)$_2$I$_2$].

EXAMPLE 9

Preparation of [(RCO)Ir(CO)$_2$I$_2$] where R = alkyl of 1 to 20 carbon atoms.

A solution of [RIr(CO)$_2$I$_2$] is prepared as described in Example 7 and treated with CO at atmospheric pressure, with R specifically being C$_8$ in one experiment and C$_{10}$ in another. Within one minute a new species is detected in solution which has strong CO stretching bands in the infrared spectrum at 2127 to 2090 cm$^{-1}$ and in addition has a strong band 1710 cm$^{-1}$ indicative of an organic acyl group (RCO—) bonded to a metal. This new species reacts with Bu$_4$N$^+$I$^-$ to give the previously characterized [(RCO)Ir(CO)$_2$I$_3$]$^-$ ion and hence the species can be formulated as [(RCO)Ir(Co)$_2$I$_2$].

EXAMPLE 10

Preparation of [Ir(norbornadiene) I]

A mixture of 2.6g of IrI$_3$3 H$_2$0, water (24 ml), ethanol (48 ml) and norbornadiene is refluxed for 16 hours under nitrogen at about 23° C. The resulting solution is cooled to 0° C and the brown precipitate which forms is filtered off, washed with methanol, and dried in vacuo, and collected as iridium norbornadiene iodide.

EXAMPLE 11

Preparation of [Ir(cyclooctatetraene)I$_3$]

A solution of 1.4g of iodine in methylene chloride (30 ml) is added to a stirred mixture of [Ir(cyclooctatetraene)] (0.9g), methylene chloride (10 ml), and cyclooctatraene (1 ml). The mixture is stirred for 20 min. at about 25° C and the resulting black powder is filtered off, washed with ethanol and air dried.

EXAMPLE 12

Preparation of [Ir(CO)$_3$I]

(Ir(1,5 hexadiene)I] in the amount of 0.1g and nonanoic acid (5 ml) is charged to a glass vessel capable of withstanding moderate pressures. The vessel is charged to 4 atmospheres pressure of carbon monoxide and the mixture stirred for 10 minutes at about 30° C. After this time the pressure is released and the brown solution examined by infrared spectrocopy, and found to contain a species with C ≡ O stretching vibrations at 2076 cm$^{-1}$ and 2042 cm$^{-1}$.

EXAMPLE 13

Method A

Preparation of [Ir(CO)$_3$I$_3$]

[Ir(cyclohexa-1,3-diene)I$_3$] in the amount of 0.2g and methylene chloride (5 ml) are charged to a small glass vessel capable of withstanding moderate pressures, and heated at 100° C under 3 atmospheres of carbon monoxide pressure for 10 minutes. The vessel is then cooled and depressurized and the resulting orange solution cooled to cyrstallize the compound.

EXAMPLE 14

Preparation of [Ir(2,5-dimethylhexa-1,5-diene)I]

A mixture of IrI$_3$.3H$_2$0 (2.6g), water (24 ), ethanol (48 ml) and 2,5-dimethylhexa-1,5-diene (5.0 ml) is refluxed for 16 hours under nitrogen. The resulting solution is cooled to 0° C and the brown precipitate which forms is filtered off, washed with methanol, and dried in vacuo, and colledted as iridium iodide.

EXAMPLE 15

A Hastelloy-C batch reactor is charged with the following ingredients: 0.5 grams of an iridium compound having the formula [Ir(cyclooctadiene)I]; 77 ml of tridecanoic acid as solvent, and 82 ml of dodecene as feed. The reactor is pressurized with carbon monoxide to a total pressure of 29 kg/cm$^2$ corresponding to a carbon monoxide partial pressure of about 26 Kg.cm$^2$ at the reaction temperature of 175° C. The reaction is carried out at constant pressure. Distilled water is pumped into the reaction during the course of the reaction. Liquid samples are removed as the reaction proceeds.

The first sample removed after 8 minutes of reaction has 53.7 weight % dodecene and 0.16 weight % water. The rate of carboxylic acid production begins at a very fast rate. After a reaction time of 42 minutes the reaction rate slows down even though gas chromatographic analysis (GC) of the liquid sample shows considerable dodecene remaining unreacted.

Addition of water produces a significant increase in the reaction rate to carboxylic acids. The next sample analyzed by GC analysis has 12.5% dodecene, less than half the olefin of the previous sample. However, the rate of tridecanoic acid production increases to 1.2 g-m/1-hr. The final sample is removed from the reactor when the rate of reaction begins to dininish.

These results establish the very high catalytic activity of the iridium cyclooctadiene iodide catalyst system for carboxylic acid production. In the similar experiments, the charging of tricarbonyliridium(I)iodide, tricarbonyldiiodohydridoiridium(III), dicarbonyldiiodohydridoiridium(III), dicarbonyldiiodohydridoaquoiridium(III), dicarbonyldiiodoalkyliridium(III), and dicarbonyldiiodoacyliridium(III), where R is an alkyl group containing 1 to 20 carbon atoms, individually as catalysts also leads to the production of carboxylic acids.

Infrared absorption spectra of the reaction solution can be carried out on samples removed from the reactor and placed in standard liquid cells at ambient conditions. The spectra are then measured on a standard infrared spectrometer such as a Beckman IR-12 spectrometer.

What is claimed is:

1. A solution of dicarbonyldiiodohydridoaquoiridium (III), [HIr(CO)$_2$I$_2$(H$_2$O)], in inert solvent.

2. A process for preparing [HIr(CO)$_2$I$_2$(H$_2$O)] consisting of mixing a solution of [Ir(cyclooctadiene)I$_3$] with a mixture of hydrogen and carbon monoxide under pressure at elevated temperature, followed by treating the resulting solution with from 1 to 5 moles of water per mole of iridium compound.

3. A process for preparing [HIr(CO)$_2$I$_2$(H$_2$O) ] consisting of mixing a solution of [Ir(cyclooctadiene)I] with carbon monoxide and then excess iodine, followed by adding thereto carbon monoxide and hydrogen under pressure at elevated temperature and subsequently treating the resulting solution with from 1 to 5 moles of water per mole of iridium compound.

* * * * *